(12) United States Patent
Hirawat et al.

(10) Patent No.: US 9,913,846 B2
(45) Date of Patent: Mar. 13, 2018

(54) COMBINATION OF A PI3 KINASE INHIBITOR WITH PACITAXEL FOR USE IN THE TREATMENT OR PREVENTION OF A CANCER OF THE HEAD AND NECK

(71) Applicant: NOVARTIS AG, Basel (CH)

(72) Inventors: Samit Hirawat, Chatham, NJ (US); Cristian Massacesi, Neuilly sur-Seine (FR); Emmanuelle di Tomaso, Lexington, MA (US)

(73) Assignee: Novartis AG, Basel (CH)

( * ) Notice: Subject to any disclaimer, the term of this patent is extended or adjusted under 35 U.S.C. 154(b) by 3 days.

(21) Appl. No.: 15/450,727

(22) Filed: Mar. 6, 2017

(65) Prior Publication Data

US 2017/0173032 A1 Jun. 22, 2017

Related U.S. Application Data

(63) Continuation of application No. 14/785,995, filed as application No. PCT/IB2014/061239 on May 6, 2014, now abandoned.

(30) Foreign Application Priority Data

May 7, 2013 (FR) ..................... 13 54211

(51) Int. Cl.
*A61K 31/5377* (2006.01)
*A61K 31/337* (2006.01)
*A61K 31/5395* (2006.01)

(52) U.S. Cl.
CPC ........ *A61K 31/5377* (2013.01); *A61K 31/337* (2013.01); *A61K 31/5395* (2013.01)

(58) Field of Classification Search
CPC .................................................. A61K 31/5377
See application file for complete search history.

(56) References Cited

FOREIGN PATENT DOCUMENTS

| EP | 2261223 A | 12/2010 |
|---|---|---|
| WO | 2009/155659 A1 | 12/2009 |
| WO | 2012/118978 A1 | 9/2012 |
| WO | WO2012118978 A1 * | 9/2012 |

OTHER PUBLICATIONS

Shyam D Rao et al: "Molecular-targeted therapies in head and neck Cancer", Seminars in Radiation Oncology, vol. 22, No. 3, Mar. 30, 2012 (Mar. 30, 2012), pp. 207-213 XP028428866.
Matthew T. Burger et al: "Identification of NVP-BKM120 as a potent, selective, orally bioavailable class I PI3 kinsae inhibitor for treating cancer", ACS Medicinal Chemistry Letters, American Chemical Society, US, vol. 2, No. 10, Oct. 13, 2011 (Oct. 13, 2011), pp. 774-779 XP002672845.
Cristian Massacesi et al: "Challenges in the clinical development of PI3K inhibitors", Annals of the New York Academy of Sicences, vol. 1280, No. 1 Mar. 1, 2013 (Mar. 1, 2013), pp. 19-23, XP055089169.
ClinicalTrials.gov: "Study of efficacy and safety of buparlisib (BKM120) plus paclitaxel versus placebo plus paclitaxel in recurrent or metastatic head and neck cancer previously pre-treated with a platinum therapy", Clinicaltrials.gov, May 8, 2013 (May 8, 2013), XP002718232, retried from the internet: URLhttp://www.clinicaltrials.gov/ct2/show/NCT01852292 [retrieved on Dec. 18, 2013].
cancer.net "Head and Neck Cancer—Risk Factors and Prevention", @ 2015 from http://www.cancer.net/cancer-types/head-and-neck-cancer/risk-factors-an-prevention, downloaded Jan. 11, 2016, pp. 1-2.
Adele Lubell, PhD.: "Targeted therapy with PI3 kinase inhibitors", Cancer Therapy Advisor, http://;www.cancertheraphyadvisor.com/general-oncology/targeted-therapy-with-pi3-kinase; @Feb. 1, 2012 downloaded Jan. 11, 2016, pp. 1-4.

* cited by examiner

*Primary Examiner* — Noble E Jarrell
*Assistant Examiner* — John S Kenyon
(74) *Attorney, Agent, or Firm* — Michelle Han (57) ABSTRACT

A pharmaceutical combination comprising (a) a phosphatidylinositol-3-kinase (PI3K) inhibitor compound of formula (I), as defined herein, or a pharmaceutically acceptable salt thereof and (b) paclitaxel or a pharmaceutically acceptable salt thereof for simultaneous, separate or sequential use, for the treatment of a cancer of the head and neck; a pharmaceutical composition comprising said combination; the use of said combination for the preparation of a medicament for the treatment of a cancer of the head and neck; a method of treating or preventing a cancer of the head and neck comprising administering a jointly therapeutically effective amount of such a combination to a subject in need thereof; and a commercial package thereof.

3 Claims, 2 Drawing Sheets

COMBINATION OF A PI3 KINASE INHIBITOR WITH PACLITAXEL FOR USE IN THE TREATMENT OR PREVENTION OF A CANCER OF THE HEAD AND NECK

FIELD OF THE INVENTION

A pharmaceutical combination comprising (a) a phosphatidylinositol-3-kinase (PI3K) inhibitor compound of formula (I), as defined herein, or a pharmaceutically acceptable salt thereof and (b) paclitaxel or a pharmaceutically acceptable salt thereof for simultaneous, separate or sequential use, for the treatment of a cancer of the head and neck; a pharmaceutical composition comprising said combination; the use of said combination for the preparation of a medicament for the treatment of a cancer of the head and neck; a method of treating or preventing a cancer of the head and neck comprising administering a jointly therapeutically effective amount of such a combination to a subject in need thereof; and a commercial package thereof.

BACKGROUND OF THE INVENTION

Cancer of the head and neck includes all cancers arising from the upper aerodigestive tract. Squamous cell carcinomas originating from mucosal surfaces represent more than 90% of cases. The incidence of head and neck squamous cell carcinoma (HNSCC) has been gradually increasing over the last three decades. It is the fifth leading cause of cancer by incidence and the sixth leading cause of cancer mortality in the world. Treatment modalities for HNSCC include surgery, radiation and chemotherapy. With advanced HNSCC, only 35% to 55% of patients survive and remain disease-free for three years, despite aggressive therapy. Locoregional recurrence develops in 30% to 40% of patients and distant metastases develop in 12% to 22%ˆ of patients. Palliative treatment of recurrent/metastatic HNSCC remains largely ineffective, and little progress has been made.

Although HNSCC can be considered a chemosensitive disease as shown by high response rates with aggressive induction therapies (e.g., combination of 5-FU, cisplatin and docetaxel, the results are poor at relapse. Despite progress in the primary treatment by combining chemotherapy, surgery, radiation therapy, and supportive care, the recurrence rate ranges from 35-50%. Patients usually relapse locally and develop symptoms such as difficulties in swallowing, eating and speaking. The median survival for patients with recurrent disease is six months and can reach 10 months in patients with good general status. Thus, improving the clinical benefit in patients with head and neck cancer is important to improve the patient's quality of life.

Currently, more effective and targeted treatments are needed for the treatment of cancers of the head and neck, particularly HNSCC.

It is believed that the combination of the compound of formula (I) and paclitaxel will provide improved and effective treatment as compared to each monotherapy for patients suffering from a cancer of the head and neck, particularly those suffering from a cancer of the head and neck or head and neck squamous cell carcinoma resistant to prior treatment with paclitaxel, fluorouracil (5-FU), platinum-based therapies, or a combination thereof.

SUMMARY OF THE INVENTION

The present invention relates to a pharmaceutical combination comprising (a) a phosphatidylinositol-3-kinase (PI3K) inhibitor compound of formula (I), as defined herein, or a pharmaceutically acceptable salt thereof and (b) paclitaxel or a pharmaceutically acceptable salt thereof, for simultaneous, separate or sequential use for the treatment or prevention of a cancer of the head and neck.

In one embodiment, the present invention further pertains to the use of a COMBINATION OF THE INVENTION for the preparation of a pharmaceutical composition or medicament for the treatment or prevention of a cancer of the head and neck.

In one embodiment, the present invention provides a pharmaceutical combination comprising (a) a phosphatidylinositol-3-kinase (PI3K) inhibitor compound of formula (I) and (b) paclitaxel, or a pharmaceutically acceptable salt thereof, for use in the treatment or prevention of a cancer of the head and neck.

In one embodiment, the present invention provides a COMBINATION OF THE INVENTION for use in the treatment or prevention of a cancer of the head and neck.

In one embodiment, the present invention relates to a method of treating or preventing a cancer of the head and neck comprising administering a jointly therapeutically effective amount of a COMBINATION OF THE INVENTION to a subject in need thereof.

In one embodiment, the present invention pertains to a pharmaceutical composition comprising a quantity of the COMBINATION OF THE INVENTION, which is jointly therapeutically effective against a cancer of the head and neck.

In one embodiment, the present invention further provides a commercial package comprising as therapeutic agents a COMBINATION OF THE INVENTION, together with instructions for simultaneous, separate or sequential administration thereof for use in the treatment or prevention of a cancer of the head and neck.

DETAILED DESCRIPTION OF THE INVENTION

The present invention relates to a pharmaceutical combination comprising (a) a phosphatidylinositol-3-kinase (PI3K) inhibitor compound of formula (I), as defined herein, or a pharmaceutically acceptable salt thereof and (b) paclitaxel or a pharmaceutically acceptable salt thereof, for simultaneous, separate or sequential use, for the treatment or prevention of a cancer of the head and neck.

The general terms used herein are defined with the following meanings, unless explicitly stated otherwise:

The terms "comprising" and "including" are used herein in their open-ended and non-limiting sense unless otherwise noted.

The terms "a" and "an" and "the" and similar references in the context of describing the invention (especially in the context of the following claims) are to be construed to cover both the singular and the plural, unless otherwise indicated herein or clearly contradicted by context. Where the plural form is used for compounds, salts, and the like, this is taken to mean also a single compound, salt, or the like.

The term "combination" or "pharmaceutical combination", as used herein, defines either a fixed combination in one dosage unit form or a kit of parts for the combined administration where the compound of formula (I), particularly Compound A, and paclitaxel may be administered independently at the same time or separately within time intervals that allow that the therapeutic agents (i.e, the compound of formula (I), particularly Compound A, and paclitaxel and pharmaceutically acceptable salts thereof) show a cooperative, e.g., synergistic, effect.

The term "pharmaceutical composition" is defined herein to refer to a mixture or solution containing at least one therapeutic agent to be administered to a subject, e.g., a mammal or human, in order to prevent or treat a particular disease or condition affecting the mammal.

The term "pharmaceutically acceptable" is defined herein to refer to those compounds, materials, compositions and/or dosage forms, which are, within the scope of sound medical judgment, suitable for contact with the tissues a subject, e.g., a mammal or human, without excessive toxicity, irritation allergic response and other problem complications commensurate with a reasonable benefit/risk ratio.

The term "a combined preparation" is defined herein to refer to especially a "kit of parts" in the sense that the therapeutic agents (a) and (b) as defined above can be dosed independently or by use of different fixed combinations with distinguished amounts of the therapeutic agents (a) and (b), i.e., simultaneously or at different time points. The parts of the kit of parts can then e.g., be administered simultaneously or chronologically staggered, that is at different time points and with equal or different time intervals for any part of the kit of parts. The ratio of the total amounts of the therapeutic agent (a) to the therapeutic agent (b) to be administered in the combined preparation can be varied, e.g., in order to cope with the needs of a patient sub-population to be treated or the needs of the single patient.

The term "combined administration" as used herein is defined to encompass the administration of the selected therapeutic agents to a single patient, and are intended to include treatment regimens in which the agents are not necessarily administered by the same route of administration or at the same time.

The term "treating" or "treatment" as used herein comprises a treatment relieving, reducing or alleviating at least one symptom in a subject or effecting a delay of progression of a cancer of the head and neck. For example, treatment can be the diminishment of one or several symptoms of a cancer of the head and neck or complete eradication of a cancer of the head and neck. Within the meaning of the present invention, the term "treat" also denotes to arrest, delay the onset (i.e., the period prior to clinical manifestation of a cancer of the head and neck) and/or reduce the risk of developing or worsening a cancer of the head and neck. The term "prevention" is used herein to mean prevent, delay or treat, or all, as appropriate, development or continuance or aggravation of a cancer of the head and neck in a subject.

The term "joint therapeutic effect" or "jointly therapeutic effective" means that the therapeutic agents may be given separately (in a chronologically staggered manner, especially a sequence-specific manner) in such time intervals that they prefer, in the warm-blooded animal, especially human, to be treated, still show a (preferably synergistic) interaction (joint therapeutic effect). Whether this is the case can, inter alia, be determined by following the blood levels, showing that both or all therapeutic agents are present in the blood of the human to be treated at least during certain time intervals.

An "effective amount" of a combination of therapeutic agents (e.g., a compound of formula (I) and paclitaxel or pharmaceutically acceptable salts thereof) is an amount sufficient to provide an observable improvement over the baseline clinically observable signs and symptoms of the cancer of the head and neck treated with the combination.

The term "subject" or "patient" as used herein includes animals, which are capable of suffering from or afflicted with a cancer of the head and neck or any disorder involving, directly or indirectly, a cancer of the head and neck. Examples of subjects include mammals, e.g., humans, dogs, cows, horses, pigs, sheep, goats, cats, mice, rabbits rats and transgenic non-human animals. In the preferred embodiment, the subject is a human, e.g., a human suffering from, at risk of suffering from, or potentially capable of suffering from cancer of the head and neck.

The term "about" or "approximately" usually means within 20%, more preferably within 10%, and most preferably still within 5% of a given value or range. Alternatively, especially in biological systems, the term "about" means within about a log (i.e., an order of magnitude) preferably within a factor of two of a given value.

The present invention relates to a pharmaceutical combination comprising (a) a phosphatidylinositol-3-kinase (PI3K) inhibitor compound of formula (I), as defined herein, or a pharmaceutically acceptable salt thereof and (b) paclitaxel or a pharmaceutically acceptable salt thereof; for simultaneous, separate or sequential use, for the treatment or prevention of a cancer of the head and neck.

WO07/084786 describes specific pyrimidine derivatives which have been found to inhibit the activity of PI3K. The compound 5-(2,6-di-morpholin-4-yl-pyrimidin-4-yl)-4-trifluoromethyl-pyridin-2-ylamine (hereinafter also referred to as "COMPOUND A") has the chemical structure of formula (I)

The compound, its salts, its utility as a PI3K inhibitor and synthesis of the compound 5-(2,6-di-morpholin-4-yl-pyrimidin-4-yl)-4-trifluoromethyl-pyridin-2-ylamine are described in WO 2007/084786, which is hereby incorporated by reference in its entirety hereto, for instance as Example 10.

The phosphatidylinositol 3-kinase inhibitor compound of formula (I) may be present in the pharmaceutical combination in the form of the free base or a pharmaceutically acceptable salt thereof. Such salts can be prepared in situ during the final isolation and purification of the compounds, or by separately reacting the base or acid functions with a suitable organic or inorganic acid or base, respectively. Suitable salts of the compound of formula (I) include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemi-sulfate, heptanoate, hexanoate, fumarate, hydrochloride, hydrobromide, hydroiodide, 2 hydroxyethanesulfonate, lactate, maleate, methanesulfonate, nicotinate, 2 naphth-alenesulfonate, oxalate, pamoate, pectinate, persulfate, 3 phenylproionate, picrate, pivalate, propionate, succinate, sulfate, tartrate, thiocyanate, p toluenesulfonate, and undecanoate. Also, the basic nitrogen-containing groups can be quaternized with such agents as alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl, and stearyl chlorides, bromides and iodides, aralkyl halides like benzyl and phenethyl bromides, and others.

Examples of acids that may be employed to form pharmaceutically acceptable acid addition salts include such inorganic acids as hydrochloric acid, hydroboric acid, nitric acid, sulfuric acid and phosphoric acid and such organic acids as formic acid, acetic acid, trifluoroacetic acid, fumaric acid, tartaric acid, oxalic acid, maleic acid, methanesulfonic acid, succinic acid, malic acid, methanesulfonic acid, benzenesulfonic acid, and p toluenesulfonic acid, citric acid, and acidic amino acids such as aspartic acid and glutamic acid.

Pharmaceutically acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine, pyridine, picoline, triethanolamine and the like, and basic amino acids such as arginine, lysine and ornithine.

In a preferred embodiment, the compound of formula (I) is in the form of its hydrochloride salt.

Paclitaxel (TAXOL®) is a natural product with antitumor activity. Paclitaxel is obtained via a semi-synthetic process from *Taxus baccata*. The chemical name for paclitaxel is $5\beta,20$-Epoxy1,2a,4,7$\beta$, 10$\beta$, 13a-hexahydroxytax-11-en-9-one 4, 10,-diacetate 2-benzoate 13-ester with (2R, 3S)—N-benzoyl-3-phenylisoserine. Also included are the generic forms of paclitaxel, as well as various dosage forms of paclitaxel. Various dosage forms of paclitaxel include, but are not limited to, albumin nanoparticle paclitaxel marketed as ABRAXANE® and ONXOL®.

Hereinafter, the pharmaceutical combination of the compound of formula (I) or a pharmaceutically acceptable salt thereof and paclitaxel will be referred to as a COMBINATION OF THE INVENTION.

Unless otherwise specified, or clearly indicated by the text, or not applicable, reference to therapeutic agents useful in the COMBINATION OF THE INVENTION includes both the free base of the compounds, and all pharmaceutically acceptable salts of the compounds.

The present invention particularly pertains to a COMBINATION OF THE INVENTION useful for separate, simultaneous or sequential administration to a subject in need thereof for treating or preventing a cancer of the head and neck.

The present invention further pertains to the use of a COMBINATION OF THE INVENTION for the preparation of a pharmaceutical composition or medicament for the treatment or prevention of a cancer of the head and neck.

The present invention relates to a method of treating or preventing a cancer of the head and neck comprising administering a jointly therapeutically effective amount of a COMBINATION OF THE INVENTION to a subject in need thereof.

The present invention further provides a commercial package comprising as therapeutic agents a COMBINATION OF THE INVENTION, together with instructions for simultaneous, separate or sequential administration thereof for use in the treatment or prevention of a cancer of the head and neck.

The present invention particularly pertains to a COMBINATION OF THE INVENTION useful for treating or preventing a cancer of the head and neck in a subject in need thereof. In this embodiment of the present invention, the COMBINATION OF THE INVENTION is used for the treatment or prevention of a cancer of the head and neck comprising administering to the subject a combination therapy, comprising an effective amount of the combination of formula (I) or a pharmaceutically acceptable salt thereof and paclitaxel. Preferably, these therapeutic agents are administered at therapeutically effective dosages which, when combined, provide a beneficial effect. The administration may be separate, simultaneous or sequential.

In one embodiment, the COMBINATION OF THE INVENTION is useful for the treatment or prevention of a cancer of the head and neck. The term "cancer of the head and neck" is used herein to mean a broad spectrum of tumors arising from the upper aerodigestive tract. Examples of such tumors include but are not limited to cancer or tumor of the oral cavity, lips, pharynx (including nasopharynx, oropharynx, and hypopharynx), larynx, paranasal sinuses, nasal cavity, throat and salivary glands. Further, depending on the tumor type and particular combination used, a decrease of the tumor volume can be obtained. The COMBINATION OF THE INVENTION disclosed herein is also suited to prevent the metastatic spread of tumors and the growth or development of micrometastases. In a preferred embodiment, the COMBINATION OF THE INVENTION disclosed herein is used for the treatment or prevention of a cancer of the head and neck.

In a further embodiment, the cancer of the head and neck is a squamous cell carcinoma. Squamous cell carcinoma of the head and neck is used herein to mean a cancer of the head and neck that begins in squamous cells. Examples of squamous cell carcinoma of the head and neck include but are not limited to squamous cell cancers or tumors of the oral cavity, lips, pharynx (including nasopharynx, oropharynx, and hypopharynx), larynx, paranasal sinuses, nasal cavity, throat and salivary glands.

In a further embodiment, the cancer of the head and neck is resistant to prior treatment with paclitaxel, fluorouracil (5-FU), and/or platinum-based therapies. The phrase "resistant to prior treatment with paclitaxel, fluorouracil (5-FU), and/or platinum-based therapies" is defined to refer to cancer or tumor progression in a patient suffering from said cancer or tumor while receiving treatment with paclitaxel, fluorouracil (5-FU), or platinum-based therapy. Examples of prior platinum-based therapies include, but are not limited to, prior treatment with cisplatin, carboplatin, oxaliplatin, or a combination thereof. The cancer is resistant to prior treatment with paclitaxel, fluorouracil (5-FU), and/or platinum-based therapies is defined as growth or progression of the cancer while exposed to paclitaxel, fluorouracil (5-FU), and/or platinum-based therapies. In a preferred embodiment, the cancer of the head and neck is a squamous cell carcinoma of the head and neck resistant to prior treatment with paclitaxel, fluorouracil (5-FU), platinum-based therapies, or a combination thereof.

In a preferred embodiment, the COMBINATION OF THE INVENTION disclosed herein is used for the treatment or prevention of a squamous cell carcinoma of the head and neck.

The COMBINATION OF THE INVENTION disclosed herein is suitable for the treatment or prevention of poor prognosis patients, especially such poor prognosis patients having a cancer of the head and neck. Thus, in a further embodiment, the cancer of the head and neck is a squamous cell carcinoma of the head and neck. In a preferred embodiment, the cancer of the head and neck is a squamous cell carcinoma of the head and neck that is resistant to prior treatment with paclitaxel, fluorouracil (5-FU), platinum-based therapies, or a combination thereof.

The COMBINATION OF THE INVENTION is particularly useful for the treatment or prevention of cancers of the head and neck having a genetic alteration of the phosphatidylinositol-3-kinase pathway such as, for example, amplification of PI3K alpha, somatic mutation of PIK3CA, germline mutations or somatic mutations of PTEN, or mutations and translocation of p85-alpha that serve to up-regulate the p85-p110 complex.

Thus, in one embodiment, the cancer of the head and neck is characterized by amplification of PI3K alpha, somatic mutation of PIK3CA, germline mutations or somatic mutations of PTEN, or mutations and translocation of p85-alpha that serve to up-regulate the p85-p110 complex.

In a further embodiment, the cancer of the head and neck is a squamous cell carcinoma of the head and neck that is resistant to prior treatment with paclitaxel, fluorouracil (5-FU), platinum-based therapies, or a combination thereof and that is characterized by amplification of PI3K alpha, somatic mutation of PIK3CA, germline mutations or somatic mutations of PTEN, or mutations and translocation of p85-alpha that serve to up-regulate the p85-p110 complex.

In one embodiment, the present invention relates to a method of treating or preventing a cancer of the head and neck comprising administering a jointly therapeutically effective amount of a COMBINATION OF THE INVENTION to a subject in need thereof. In each embodiment, it is understood that a subject in need of a particular treatment includes subjects suffering from or diagnosed with the identified cancer of the head and neck in such embodiment.

In a further embodiment, the present invention relates to a method of treating or preventing a cancer of the head and neck characterized by amplification of PI3K alpha, somatic mutation of PIK3CA, germline mutations or somatic mutations of PTEN, or mutations and translocation of p85-alpha, comprising administering a jointly therapeutically effectively amount of a COMBINATION OF THE INVENTION to a subject in need thereof.

In a further embodiment, the present invention relates to a method of treating or preventing a cancer of the head and neck resistant to prior treatment with paclitaxel, fluorouracil (5-FU), platinum-based therapies, or a combination thereof comprising administering a jointly therapeutically effectively amount of a COMBINATION OF THE INVENTION to a subject in need thereof. In each embodiment, it is understood that a subject in need of a particular treatment includes subjects suffering from or diagnosed with the identified cancer of the head and neck in such embodiment.

In one embodiment, the present invention relates to a method of treating or preventing a squamous cell carcinoma of the head and neck comprising administering a jointly therapeutically effective amount of a combination of: (a) a compound of formula (I) or a pharmaceutically acceptable salt thereof, and (b) paclitaxel, to a subject in need thereof.

In a further embodiment, the present invention relates to a method of treating or preventing a squamous cell carcinoma of the head and neck characterized by amplification of PI3K alpha, somatic mutation of PIK3CA, germline mutations or somatic mutations of PTEN, or mutations and translocation of p85-alpha, comprising administering a jointly therapeutically effectively amount of a COMBINATION OF THE INVENTION to a subject in need thereof.

In a further embodiment, the present invention relates to a method of treating or preventing a squamous cell carcinoma of the head and neck resistant to prior treatment with paclitaxel, fluorouracil (5-FU), platinum-based therapies, or a combination thereof, comprising administering a jointly therapeutically effective amount of a combination of: (a) a compound of formula (I) or a pharmaceutically acceptable salt thereof, and (b) paclitaxel, to a subject in need thereof.

The nature of cancer is multifactorial. Under certain circumstances, drugs with different mechanisms of action may be combined. However, just considering any combination of therapeutic agents having different mode of action does not necessarily lead to combinations with advantageous effects.

The administration of a pharmaceutical combination of the invention may result not only in a beneficial effect, e.g. a synergistic therapeutic effect, e.g. with regard to alleviating, delaying progression of or inhibiting the symptoms, but also in further surprising beneficial effects, e.g. fewer side-effects, more durable response, an improved quality of life or a decreased morbidity, compared with a monotherapy applying only one of the pharmaceutically therapeutic agents used in the combination of the invention.

Preferably, there is at least one beneficial effect, e.g., a mutual enhancing of the effect of the therapeutic agent (a) and (b), in particular a synergism (e.g., a more than additive effect), additional advantageous effects, less side effects, a combined therapeutic effect in a non-effective dosage of one or both of the therapeutic agent (a) and (b), and very preferably a strong synergism of the therapeutic agent (a) and (b).

The term "synergistic effect" or "synergism" as used herein, refers to action of two therapeutic agents such as, for example, a compound of formula (I), e.g., compound A, and paclitaxel, producing an effect, for example, slowing the symptomatic progression of a proliferative disease or symptoms thereof, which is greater than the simple addition of the effects of each drug administered by themselves. A synergistic effect can be calculated, for example, using suitable methods such as the Sigmoid-Emax equation (Holford, N. H. G. and Scheiner, L. B., Clin. Pharmacokinet. 6: 429-453 (1981)), the equation of Loewe additivity (Loewe, S. and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984)). Each equation referred to above can be applied to experimental data to generate a corresponding graph to aid in assessing the effects of the drug combination. The corresponding graphs associated with the equations referred to above are the concentration-effect curve, isobologram curve and combination index curve, respectively.

It can be shown by established test models that a COMBINATION OF THE INVENTION results in the beneficial effects described herein before. The person skilled in the art is fully enabled to select a relevant test model to prove such beneficial effects. The pharmacological activity of a COMBINATION OF THE INVENTION may, for example, be demonstrated in a clinical study or in an animal model as essentially described hereinafter.

Determining a synergistic interaction between one or more components, the optimum range for the effect and absolute dose ranges of each component for the effect may be definitively measured by administration of the components over different w/w ratio ranges and doses to patients in need of treatment. For humans, the complexity and cost of carrying out clinical studies on patients may render impractical the use of this form of testing as a primary model for synergy. However, the observation of synergy in one species can be predictive of the effect in other species and animal models exist, as described herein, to measure a synergistic effect and the results of such studies can also be used to predict effective dose ratio ranges and the absolute doses and plasma concentrations required in other species by the application of pharmacokinetic/pharmacodynamic methods. Established correlations between tumor models and effects seen in man suggest that synergy in animals may be demonstrated, for example, by xenograft models or in appropriate cell lines.

Suitable clinical studies are, for example, open label non-randomized, dose escalation studies or multi-center, randomized, double-blind, placebo-controlled studies in patients with a cancer of the head and neck. Such studies can prove the additive or synergism of the active ingredients of the COMBINATIONS OF THE INVENTION. The beneficial effects on proliferative diseases can be determined directly through the results of these studies or by changes in the study design which are known as such to a person skilled in the art. Such studies are, in particular, suitable to compare the effects of a monotherapy using the active ingredients and a COMBINATION OF THE INVENTION. Preferably, the therapeutic agent (a) is administered with a fixed dose and the dose of the therapeutic agent (b) is escalated until the Maximum Tolerated Dosage is reached.

The compound of formula (I) is preferably administered daily at a dose in the range of from 1.0 to 30 mg/kg body weight. In one preferred embodiment, the dosage of compound of formula (I) is in the range of about 60 mg/day to about 120 mg/day, especially if the warm-blooded animal is an adult human. Preferably, the dosage of compound of formula (I) is in the range of about 80 mg/day to about 100 mg/day for an adult human. The Compound of formula (I) may be administered orally to an adult human once daily continuously (each day) or intermittently (e.g. 5 out of 7 days) in a suitable dosage.

For paclitaxel, the dose range in the adult human suitably corresponds to a dose range of about 15 to 200 mg/m$^2$, e.g., about 50 to 175 mg/m$^2$, about 60 to 100 mg/m$^2$, or about 70 to 100 mg/m$^2$ per week. Preferably, the dose is 80 mg/m$^2$ per week.

In one embodiment, the present invention pertains to a pharmaceutical composition or combined preparation comprising a jointly therapeutically effective amount of the COMBINATION OF THE INVENTION and optionally at least one pharmaceutically acceptable carrier, for use in the treatment or prevention of a cancer of the head and neck. In this composition or combined preparation, the therapeutic agents of the compound of formula (I), particularly COMPOUND A, or a pharmaceutically acceptable salt thereof and paclitaxel can be administered together in a single formulation or unit dosage form, administered concurrently but separately, or sequentially by any suitable route.

A therapeutically effective amount of the therapeutic agents of the COMBINATION OF THE INVENTION may be administered simultaneously or sequentially and in any order, and the components may be administered separately or as a fixed combination. For example, the method of treatment or prevention of a cancer of the head and neck according to the invention may comprise (i) administration of the first therapeutic agent in free or pharmaceutically acceptable salt form and (ii) administration of the second therapeutic agent in free or pharmaceutically acceptable salt form, simultaneously or sequentially in any order, in jointly therapeutically effective amounts, preferably in synergistically effective amounts. The individual therapeutic agents of the COMBINATION OF THE INVENTION can be administered separately at different times during the course of therapy or concurrently in divided or single combination forms. The invention is therefore to be understood as embracing all such regimens of simultaneous or alternating treatment and the term "administering" is to be interpreted accordingly. Preferably, the compound of formula (I) and paclitaxel are administered separately.

The pharmaceutical compositions according to the invention can be prepared in a manner known per se and are those suitable for enteral, such as oral or rectal, and parenteral administration to mammals (warm-blooded animals), including man. Alternatively, when the agents are administered separately, one can be an enteral formulation and the other can be administered parenterally.

The novel pharmaceutical composition contain, for example, from about 10% to about 100%, preferably from about 20% to about 60%, of the active ingredients. Pharmaceutical preparations for the combination therapy for enteral or parenteral administration are, for example, those in unit dosage forms, such as sugar-coated tablets, tablets, capsules or suppositories, and furthermore ampoules. If not indicated otherwise, these are prepared in a manner known per se, for example by means of conventional mixing, granulating, sugar-coating, dissolving or lyophilizing processes. It will be appreciated that the unit content of one of the therapeutic agents contained in an individual dose of each dosage form need not in itself constitute an effective amount since the necessary effective amount can be reached by administration of a plurality of dosage units.

In preparing the compositions for oral dosage form, any of the usual pharmaceutically acceptable carriers may be employed, such as, for example, water, glycols, oils, alcohols, flavoring agents, preservatives, coloring agents; or carriers such as starches, sugars, microcristalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed.

One of ordinary skill in the art may select one or more of the aforementioned carriers with respect to the particular desired properties of the dosage form by routine experimentation and without any undue burden. The amount of each carriers used may vary within ranges conventional in the art. The following references which are all hereby incorporated by reference disclose techniques and excipients used to formulate oral dosage forms. See The Handbook of Pharmaceutical Excipients, 4$^{th}$ edition, Rowe et al., Eds., American Pharmaceuticals Association (2003); and *Remington: the Science and Practice of Pharmacy*, 20$^{th}$ edition, Gennaro, Ed., Lippincott Williams & Wilkins (2003).

Examples of pharmaceutically acceptable disintegrants include, but are not limited to, starches; clays; celluloses;

alginates; gums; cross-linked polymers, e.g., cross-linked polyvinyl pyrrolidone or crospovidone, e.g., POLYPLASDONE XL from International Specialty Products (Wayne, N.J.); cross-linked sodium carboxymethylcellulose or croscarmellose sodium, e.g., AC-DI-SOL from FMC; and cross-linked calcium carboxymethylcellulose; soy polysaccharides; and guar gum. The disintegrant may be present in an amount from about 0% to about 10% by weight of the composition. In one embodiment, the disintegrant is present in an amount from about 0.1% to about 5% by weight of composition.

Examples of pharmaceutically acceptable binders include, but are not limited to, starches; celluloses and derivatives thereof, for example, microcrystalline cellulose, e.g., AVICEL PH from FMC (Philadelphia, Pa.), hydroxypropyl cellulose hydroxyethyl cellulose and hydroxylpropylmethyl cellulose METHOCEL from Dow Chemical Corp. (Midland, Mich.); sucrose; dextrose; corn syrup; polysaccharides; and gelatin. The binder may be present in an amount from about 0% to about 50%, e.g., 2-20% by weight of the composition.

Examples of pharmaceutically acceptable lubricants and pharmaceutically acceptable glidants include, but are not limited to, colloidal silica, magnesium trisilicate, starches, talc, tribasic calcium phosphate, magnesium stearate, aluminum stearate, calcium stearate, magnesium carbonate, magnesium oxide, polyethylene glycol, powdered cellulose and microcrystalline cellulose. The lubricant may be present in an amount from about 0% to about 10% by weight of the composition. In one embodiment, the lubricant may be present in an amount from about 0.1% to about 1.5% by weight of composition. The glidant may be present in an amount from about 0.1% to about 10% by weight.

Examples of pharmaceutically acceptable fillers and pharmaceutically acceptable diluents include, but are not limited to, confectioner's sugar, compressible sugar, dextrates, dextrin, dextrose, lactose, mannitol, microcrystalline cellulose, powdered cellulose, sorbitol, sucrose and talc. The filler and/or diluent, e.g., may be present in an amount from about 0% to about 80% by weight of the composition.

The effective dosage of each of the therapeutic agents employed in the COMBINATION OF THE INVENTION may vary depending on the particular compound or pharmaceutical composition employed, the mode of administration, the condition being treated, and the severity of the condition being treated. Thus, the dosage regimen of the COMBINATION OF THE INVENTION is selected in accordance with a variety of factors including the route of administration and the renal and hepatic function of the patient. A clinician or physician of ordinary skill can readily determine and prescribe the effective amount of the single therapeutic agents required to alleviate, counter or arrest the progress of the condition.

The optimum ratios, individual and combined dosages, and concentrations of the therapeutic agents (a) and (b) and optionally (c) of the COMBINATION OF THE INVENTION that yield efficacy without toxicity are based on the kinetics of the therapeutic agents' availability to target sites, and are determined using methods known to those of skill in the art.

The effective dosage of each of the therapeutic agents may require more frequent administration of one of the compound(s) as compared to the other compound(s) in the combination. Therefore, to permit appropriate dosing, packaged pharmaceutical products may contain one or more dosage forms that contain the combination of compounds, and one or more dosage forms that contain one of the combination of compounds, but not the other compound(s) of the combination.

When the therapeutic agents, which are employed in the COMBINATION OF THE INVENTION, are applied in the form as marketed as single drugs, their dosage and mode of administration can be in accordance with the information provided on the package insert of the respective marketed drug, if not mentioned herein otherwise.

The optimal dosage of each therapeutic agents for treatment or prevention of a proliferative disease can be determined empirically for each individual using known methods and will depend upon a variety of factors, including, though not limited to, the degree of advancement of the disease; the age, body weight, general health, gender and diet of the individual; the time and route of administration; and other medications the individual is taking. Optimal dosages may be established using routine testing and procedures that are well known in the art.

The amount of each therapeutic agent of the COMBINATION OF THE INVENTION that may be combined with the carrier materials to produce a single dosage form will vary depending upon the individual treated and the particular mode of administration. In some embodiments the unit dosage forms containing the combination of agents as described herein will contain the amounts of each therapeutic agent of the combination that are typically administered when the therapeutic agents are administered alone.

Frequency of dosage may vary depending on the therapeutic agent used and the particular condition to be treated or prevented. Patients may generally be monitored for therapeutic effectiveness using assays suitable for the condition being treated or prevented, which will be familiar to those of ordinary skill in the art.

In one embodiment, the present invention pertains to the use of a COMBINATION OF THE INVENTION for the treatment or prevention of a cancer of the head and neck.

In a further embodiment, the present invention pertains to the use of a COMBINATION OF THE INVENTION for the treatment or prevention of a cancer of the head and neck resistant to prior treatment with paclitaxel, fluorouracil (5-FU), platinum-based therapies, or a combination thereof.

In a further embodiment, the present invention pertains to the use of a COMBINATION OF THE INVENTION for the treatment or prevention of a squamous cell carcinoma of the head and neck.

In a preferred embodiment, the present invention pertains to the use of the pharmaceutical combination comprising COMPOUND A or a pharmaceutically acceptable salt thereof and paclitaxel or a pharmaceutically acceptable salt thereof for the treatment or prevention of a squamous cell carcinoma of the head and neck. Preferably, the squamous cell carcinoma of the head and neck is resistant to prior treatment with paclitaxel, fluorouracil (5-FU), platinum-based therapies, or a combination thereof.

In one embodiment, the present invention pertains to the use of a COMBINATION OF THE INVENTION for the preparation of a medicament for the treatment or prevention of a cancer of the head and neck.

In a further embodiment, the present invention pertains to the use of a COMBINATION OF THE INVENTION for the preparation of a medicament for the treatment or prevention of a cancer of the head and neck resistant to prior treatment with paclitaxel, fluorouracil (5-FU), platinum-based therapies, or a combination thereof.

In a further embodiment, the present invention pertains to the use of a COMBINATION OF THE INVENTION for the preparation of a medicament for the treatment or prevention of a squamous cell carcinoma of the head and neck.

In a further embodiment, the present invention pertains to the use of a COMBINATION OF THE INVENTION for the preparation of a medicament for the treatment or prevention of a squamous cell carcinoma of the head and neck resistant to prior treatment with paclitaxel, fluorouracil (5-FU), platinum-based therapies, or a combination thereof.

In a preferred embodiment, the present invention pertains to the use of the pharmaceutical combination comprising COMPOUND A or a pharmaceutically acceptable salt thereof and paclitaxel or a pharmaceutically acceptable salt thereof for the preparation of a medicament for the treatment or prevention of a squamous cell carcinoma of the head and neck. Preferably, the squamous cell carcinoma of the head and neck is resistant to prior treatment with paclitaxel, fluorouracil (5-FU), platinum-based therapies, or a combination thereof.

Moreover, the present invention provides a commercial package comprising as active ingredients of COMBINATION OF THE INVENTION, together with instructions for simultaneous, separate or sequential administration thereof for use in the treatment or prevention of a cancer of the head and neck.

In a further embodiment, the present invention provides a commercial package comprising as active ingredients of COMBINATION OF THE INVENTION, together with instructions for simultaneous, separate or sequential administration thereof for use in the treatment or prevention of a cancer of the head and neck resistant to prior treatment with paclitaxel, fluorouracil (5-FU), platinum-based therapies, or a combination thereof.

In further aspects, the present inventions provides
- a pharmaceutical combination which comprises (a) a COMBINATION OF THE INVENTION, wherein the active ingredients are present in each case in free form or in the form of a pharmaceutically acceptable salt, and optionally at least one pharmaceutically acceptable carrier; for simultaneous, separate or sequential use for the treatment or prevention of a cancer of the head and neck;
- a pharmaceutical combination which comprises (a) a COMBINATION OF THE INVENTION, wherein the active ingredients are present in each case in free form or in the form of a pharmaceutically acceptable salt, and optionally at least one pharmaceutically acceptable carrier; for simultaneous, separate or sequential use for the treatment or prevention of a cancer of the head and neck resistant to prior treatment with paclitaxel, fluorouracil (5-FU), platinum-based therapies, or a combination thereof;
- a pharmaceutical composition comprising a quantity which is jointly therapeutically effective against a cancer of the head and neck of a COMBINATION OF THE INVENTION and at least one pharmaceutically acceptable carrier;
- a pharmaceutical composition comprising a quantity, which is jointly therapeutically effective against a cancer of the head and neck resistant to prior treatment with paclitaxel, fluorouracil (5-FU), platinum-based therapies, or a combination thereof, of a COMBINATION OF THE INVENTION and at least one pharmaceutically acceptable carrier;
- a combined preparation comprising (a) one or more unit dosage forms of a therapeutic compound of formula (I) or a pharmaceutically acceptable salt thereof and (b) paclitaxel or a pharmaceutically acceptable salt thereof for use in the treatment or prevention of a cancer of the head and neck;
- a combined preparation comprising (a) one or more unit dosage forms of a therapeutic compound of formula (I) or a pharmaceutically acceptable salt thereof and (b) paclitaxel or a pharmaceutically acceptable salt thereof for use in the treatment or prevention of a cancer of the head and neck resistant to prior treatment with paclitaxel, fluorouracil (5-FU), platinum-based therapies, or a combination thereof.

The following Examples illustrate the invention described above; they are not, however, intended to limit the scope of the invention in any way. The beneficial effects of the COMBINATION OF THE INVENTION can also be determined by other test models known as such to the person skilled in the pertinent art.

Figure 1:
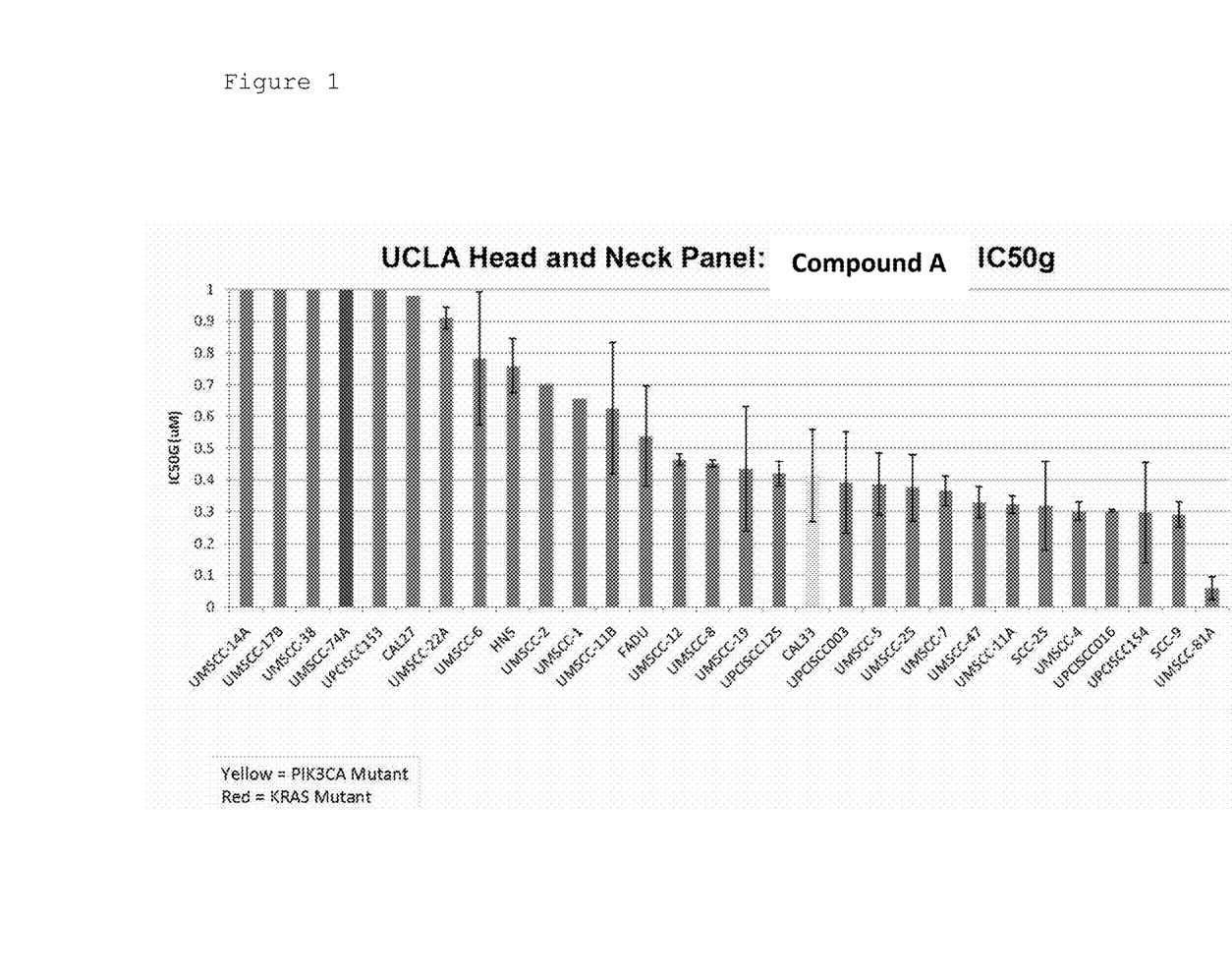
FIG. 1 shows the IC50 values for Compound A for several cancer cell lines.

Example 1: Sensitivity of Head and Neck Cancer Cell Lines to Compound A and to a Combination of Paclitaxel and Compound A As shown in FIG. 1, two panels were independently tested for sensitivity to Compound A. The majority of the cell lines display an IC50 below 1 µM in line with clinically relevant concentrations (concentration delivered to patients treated at 100 mg daily is expected to be around 1 µM). (Red=KRAS mutant=UMSCC-74A. Yellow=PI3KCA mutant=CAL33).

Figure 2:
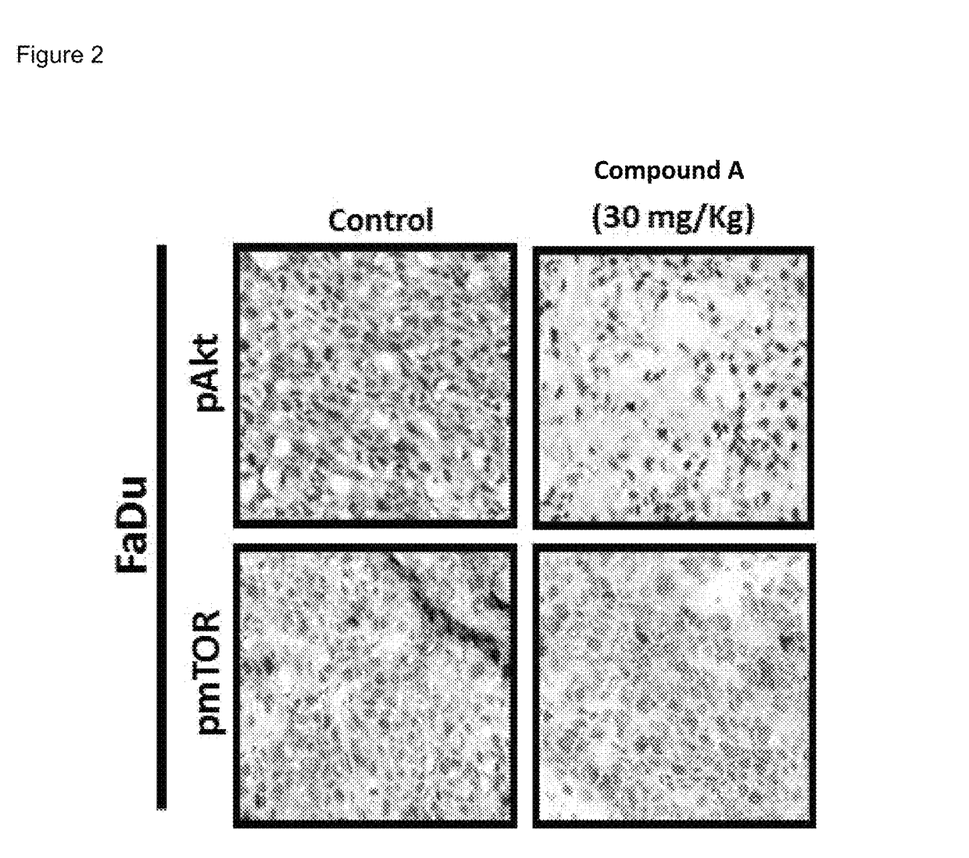
FIG. 2 shows the results of administration of Compound A in squamous cancer cells.

As shown in FIG. 2, treatment of FaDu xenograft (Hypopharynx squamous cell carcinoma) with Compound A at 30 mg daily (equivalent to 100 mg daily in patients) shows inhibition of pAKT in tumor tissue confirming down-regulation of the PI3K pathway upon treatment. Treatment with Paclitaxel and Compound A in head and neck cancer cell lines displays combination effect with potential for synergy in some cases. Cells were plated in 24-well plates at a density of 5×104 to 1×105 cells per well and grown in DMEM with 10% FBS and 1% PSF. The day after plating (day 1), Compound A—1 µmol/L was serially diluted 10-fold over 6 concentrations, and drug was added alone or in combination with a single concentration of paclitaxel 1 ng/mL. Data was compared with untreated controls. Cells were counted on the day drug was added and 5 days later and these 2 counts were compared. Cells were harvested by trypsinization and counted immediately using a Coulter Z2 particle counter (Beckman Coulter Inc., Fullerton, Calif., USA). Percentage of growth inhibition, defined as 100×[1−(generations in treated wells/generations in untreated controls)] was determined, as previously published (Finn, et al, 2009). Experiments were carried out in duplicate. The table below details the results.

TABLE 1

Cancer Cell Growth Inhibition

| | % cell growth inhibition | | |
|---|---|---|---|
| Cell line | Paclitaxel (1 ng/ml) | Compound A (1 µM) | Combination of Compound A and Paclitaxel |
| UMSCC5 | 7.6% | 28% | 28% |
| UMSCC1 | 4.6% | 21.2% | 48.5% |
| UMSCC11A | 3.13% | 21.92% | 27.95% |
| UPCISCC153 | 0.0% | 15.02% | 16.79% |

Example 2: Clinical Study

A clinical study using (a) a phosphatidylinositol 3-kinase inhibitor COMPOUND A or its hydrochloride salt, in combination with (b) paclitaxel for treatment of patients with recurrent or metastatic HNSCC cancer that has progressed after prior platinum based treatment regimen.

A multi-center, randomized, double-blind, placebo-controlled phase II trial of the combination comprising (a) COMPOUND A or its hydrochloride salt and (b) paclitaxel is conducted in patients with recurrent or metastatic HNSCC cancer that has progressed after prior platinum based treatment regimen. Patients with histologically/cytologically-confirmed HNSCC, recurrent or metastatic disease progressing after prior platinum-based first-line treatment will be randomized in a 1:1 ratio to 2 different clinical group arms to receive in a blinded manner one of two treatments: (a) COMPOUND A or its hydrochloride salt in combination with paclitaxel, or (b) placebo in combination with paclitaxel. Approximately 150 will be enrolled in the study, but the effectiveness of the combination treatment may be assessed with results from fewer total patients. Patients may be stratified according to the number of prior lines of treatment (1 vs. 2) and the region of the investigator's site. Patients are continuing to receive study treatment according to randomization until disease progression (assessed by RECIST 1.1), unacceptable toxicity, death or discontinuation from study treatment for any other reason (e.g., withdrawal of consent, start of a new neoplastic therapy or at the discretion of the investigator). Efficacy and safety monitoring will continue as per visit schedule. Tumor assessments will be performed 4 weeks after study treatment start and afterwards every 6 weeks until radiological progression.

For the clinical study "progressed after prior platinum based treatment regimen" is defined as progression while on platinum-based chemotherapy given in the recurrent/metastatic setting.

The following inclusion and exclusion criteria define those patients eligible for the study:

Inclusion Criteria:

Patients eligible for inclusion in this study are meeting all of the following criteria:
1. Patient is ≥18 years old;
2. Written informed consent obtained before any trial related activities and according to local guidelines.
3. Patient has histologically/cytologically-confirmed HNSCC.
4. Patient has archival or fresh tumor tissue for the analysis of PI3K-related biomarkers.
5. Patients with recurrent or metastatic disease resistant to platinum-based chemotherapy (defined as progression while on platinum-based chemotherapy given in the recurrent/metastatic setting). Pretreatment with cetuximab (as part of chemoradiation, first-line therapy or maintenance, or as single agent second line regimen) is allowed
6. Measurable disease as determined by per RECIST criteria v1.1. If the only site of measurable disease is a previously irradiated lesion, documented progression of disease and a 4 week period since radiotherapy completion is required
7. Adequate bone marrow function and organ function as shown by:
    Absolute neutrophil count (ANC)≥1.5×10$^9$/L
    Hemoglobin ≥9 g/dl (which may be reached by transfusion)
    Platelets ≥100×10$^9$/L (which may be reached by transfusion)
    INR ≤1.5
    Potassium, calcium (corrected for serum albumin) and magnesium within normal limits (WNL) for the institution
    Alanine aminotransferase (AST) and aspartate aminotransferase (ALT) below or equal upper limit of normal range (or <3.0×ULN if liver metastases are present)
    Total serum bilirubin below or equal upper limit of normal range (or ≤1.5×ULN if liver metastases are present; or total bilirubin ≤3.0×ULN with direct bilirubin below or within normal range in patients with well documented Gilbert's Syndrome, which is defined as presence of episodes of unconjugated hyperbilirubinemia with normal results from CBC count (including normal reticulocyte count and blood smear), normal liver function test results, and absence of other contributing disease processes at the time of diagnosis (see Appendix in the final protocol)
    Serum creatinine ≤1.5×ULN or calculated or directly measured CrCl≥50% LLN (Lower Limit of Normal)
    Fasting plasma glucose (FPG)≤120 mg/dL or ≤6.7 mmol/L
    HbA1c≤8%
8. ECOG Performance Status 1
9. Patient is able to swallow and retain oral medication (including patients able to swallow oral medication but mostly self-nourished through gastric or jejunal feeding tube).

Exclusion Criteria:

Patients eligible for this study do not meet any of the following criteria:
1. Patient has received previous treatment with any AKT, mammalian target of rapamycin (mTOR) inhibitors or phosphatidylinositol 3-kinase (PI3K) pathway inhibitors;
2. Patient received treatment with a taxane as part prior treatment for metastatic disease;
3. Patient treated with more than one prior chemotherapy regimen for recurrent/metastatic disease (i.e. chemotherapy, chemotherapy in association with a biologic/targeted agent). However, patients treated with adjuvant/neoadjuvant chemotherapy and/or concomitant chemoradiotherapy regimen that may have included biologic/targeted agent are eligible and cetuximab single agent used in metastatic setting is allowed.
4. Patient has symptomatic CNS metastases. Patients with asymptomatic CNS metastases may participate in this trial. The patient must have completed any prior local treatment for CNS metastases 28 days prior to the start of study treatment (including radiotherapy and/or surgery) and must have stable low dose of corticosteroid therapy;
5. Patient who has received wide field radiotherapy 4 weeks or limited field radiation for palliation ≤2 weeks prior to starting study drug or who have not recovered to grade 1 or better from related side effects of such therapy (except alopecia)
6. Patient has not recovered to grade 1 or better (except alopecia) from related side effects of any prior antineoplastic therapy
7. Patient has had major surgery within 14 days prior to starting study drug or has not recovered from major side effects
8. Patient is currently receiving increasing or chronic treatment (>5 days) with corticosteroids or another immunosuppressive agent, as chronic administration of corticosteroids (>5 days) can induce CYP3A4
   The following uses of corticosteroids are permitted: single doses; standard premedication for paclitaxel; topical applications (e.g., rash), inhaled sprays (e.g., obstructive airways diseases), eye drops or local injections (e.g., intra-articular)
9. Patient is being treated at start of study treatment with any of the following drugs:
   Drugs known to be moderate and strong inhibitors or inducers of isoenzyme CYP3A4 including herbal medications (list of prohibited CYP3A4 inhibitors and inducers to be provided in final protocol)
   Drugs with a known risk to induce Torsades de Pointes
   Note: The patient must have discontinued strong inducers for at least one week and must have discontinued strong inhibitors before the treatment is initiated. Switching to a different medication prior to starting study treatment is allowed.
10. Patient is currently receiving warfarin or other coumarin derived anti-coagulant, for treatment, prophylaxis or otherwise. Therapy with heparin, low molecular weight heparin (LMWH), or fondaparinux is allowed;
11. Patient has a known hypersensitivity and/or contra indication to paclitaxel, standard pre-treatment for paclitaxel or other products containing Cremophor;
12. Patients who have other concurrent severe and/or uncontrolled medical conditions that would, in the investigator's judgment, contraindicate patient participation in the clinical study (eg. active or uncontrolled severe infection, chronic active hepatitis, immunocompromised, acute or chronic pancreatitis, uncontrolled high blood pressure, interstitial lung disease, etc.)
13. Patient has a known history of HIV infection (testing not mandatory) infection
14. Patient has any of the following cardiac abnormalities:
   symptomatic congestive heart failure,
      history of documented congestive heart failure (New York Heart Association functional classification III-IV), documented cardiomyopathy,
      Left Ventricular Ejection Fraction (LVEF)<50% as determined by Multiple Gated acquisition (MUGA) scan or echocardiogram (ECHO)
   myocardial infarction 6 months prior to enrolment,
   unstable angina pectoris,
   serious uncontrolled cardiac arrhythmia,
   symptomatic pericarditis,
   QTcF>480 msec on the screening ECG (using the QTcF formula)
   currently receiving treatment with medication that has a known risk to prolong the QT interval or inducing Torsades de Pointes, and the treatment cannot be discontinued or switched to a different medication prior to starting study drug. A list of prohibited drugs will be provided in the final protocol;
15. Patient has impairment of gastrointestinal (GI) function or GI disease that may significantly alter the absorption of study drug (e.g., ulcerative diseases, uncontrolled nausea, vomiting, diarrhea, malabsorption syndrome, or small bowel resection);
16. Patient has a score 12 on the PHQ-9 questionnaire;
17. Patient selects a response of "1, 2 or 3" to question number 9 on the PHQ-9 questionnaire regarding potential for suicidal thoughts or ideation (independent of the total score of the PHQ-9);
18. Patient has a GAD-7 mood scale score 15;
19. Patient has a medically documented history of or active major depressive episode, bipolar disorder (I or II), obsessive-compulsive disorder, schizophrenia, a history of suicidal attempt or ideation, or homicidal ideation (e.g. risk of doing harm to self or others); or patients with active severe personality disorders (defined according to DSM-IV) are not eligible. Note: for patients with psychotropic treatments ongoing at baseline, the dose and the schedule should not be modified within the previous 6 weeks prior to start of study drug.
20. Patient has ≥CTCAE grade 3 anxiety;
21. Patient has other prior or concurrent malignancy (except for the following: adequately treated basal cell or squamous cell skin cancer, or other adequately treated in situ cancer, or any other cancer from which the patient has been disease free for 3 years);
22. Patient has a history of non-compliance to medical regimen or inability to grant consent;
23. Patient is concurrently using other approved or investigational antineoplastic agent.
24. Pregnant or nursing (lactating) women, where pregnancy is defined as the state of a female after conception and until the termination of gestation, confirmed by a positive hCG laboratory test (>5 mIU/mL). Patients with elevated hCG at baseline that is judged to be related to the tumor are eligible if hCG levels do not show the expected doubling when repeated 5-7 days later, or pregnancy has been ruled out by vaginal ultrasound;
25. Patient who does not apply highly effective contraception during the study and through the duration as defined below after the final dose of study treatment:
   Men should use an effective method of contraception and not father a child during the trial and up to six months after treatment and are recommended to seek advice on conservation of sperm prior to treatment with paclitaxel as per product label.
   Women of child-bearing potential, defined as all women physiologically capable of becoming pregnant, must use highly effective contraception during the study and through at least 4 weeks after the final dose of study treatment or as specified in the local prescription guidelines for paclitaxel (e.g. for 6 months after final dose of paclitaxel according to the PI/SmPC from France and United Kingdom).
   Highly effective contraception is defined as either:
   1. Total abstinence: When this is in line with the preferred and usual lifestyle of the subject. [Periodic abstinence (e.g., calendar, ovulation, symptothermal, post-ovulation methods) and withdrawal are not acceptable methods of contraception].
   2. Female sterilization: have had surgical bilateral oophorectomy (with or without hysterectomy) or tubal ligation at least six weeks before taking study treatment. In case of oophorectomy alone, only when the reproductive status of the woman has been confirmed by follow up hormone level assessment
   3. Male partner sterilization (with the appropriate post-vasectomy documentation of the absence of sperm in the ejaculate). [For female study subjects, the vasectomized male partner should be the sole partner for that patient]
   4. Use a combination of the following (both a+b):
      a. Placement of an intrauterine device (IUD) or intrauterine system (IUS)

b. Barrier methods of contraception: Condom or Occlusive cap (diaphragm or cervical/vault caps) with spermicidal foam/gel/film/cream/vaginal suppository.

Note: Hormonal contraception methods (e.g. oral, injected, implanted) are not allowed as COMPOUND A decreases the effectiveness of hormonal contraceptives.

Women are considered post-menopausal and not of childbearing potential if they have had 12 months of natural (spontaneous) amenorrhea with an appropriate clinical profile (e.g. age appropriate, history of vasomotor symptoms) or have had surgical bilateral oophorectomy (with or without hysterectomy) at least six weeks ago. In the case of oophorectomy alone, only when the reproductive status of the woman has been confirmed by follow up hormone level assessment is she considered not of child bearing potential.

Screening is conducted within 1 to 35 days prior to treatment start (except for radiological tumor assessments which are done within 1 to 28 days prior to treatment start). Rescreening is permitted only once per patient if the patient was not registered as entering treatment phase. Repeat laboratory evaluations within the screening window is permitted for screening results out of the defined range.

The primary objective is to estimate treatment effect of the combination of once-daily Compound A or its hydrochloride salt and paclitaxel on progression-free survival (PFS) (based on local radiological assessment) in these above-identified patients. A primary efficacy variable is progression free survival as assessed by local radiological reviewed as per RECIST v 1.1. PFS is defined as the time from the randomization date until objective tumor progression or death from any cause. The date of progression is the earlier time when any RECIST progression event (i.e, radiological progression or death) is observed with no more than one prior missing assessment.

Tumor evaluations are made based on RECIST criteria. In evaluating the tumors, measurability is defined as the presence of at least one measurable nodal or non-nodal lesion and, if restricted to a solitary lesion, its neoplastic nature sure be confirmed by cytology/histology.

Secondary objectives include assessment of overall survival (time from randomization to date of death due to any cause), overall response rate (the ortion of patients with a best overall response of complete response (CR) or partial response (PR) based on investigator assessment); disease control rate (the proportion of patients with a best overall response of CR, PR or stable disease (SD), based on investigator assessment, and duration of response (defined only for the responder subset, i.e., patients with confirmed CR or PR based on investigator assessment. This is the elapsed time between the date of first documented response and the following date of event defined as the first documented progression or death due to underlying cancer).

After screening, patients are randomized into one of the two treatment groups and such randomization is kept confidential. Patients are treated with either: (a) Compound A or its hydrochloride salt and paclitaxel, or (b) COMPOUND A-matching placebo and paclitaxel until disease progression, unaccepted toxicity, death or discontinuation from the study for any other reason. Visits and associated assessments that deviate +/−3 days of scheduled date (except Day1) are not protocol deviations. MRI/CT scans are performed at Cycle 2 Day 1 (+/−3 days) and every 6 weeks (+/−4 days) until disease progression, withdrawal consent, lost to follow-up, start of another anti-neoplastic therapy, or death, whichever occurs first. Laboratory assessments performed as part of the screening evaluation and within 7 days of first dose of study treatment are not required to be repeated on first dosing day.

COMPOUND A or its hydrochloride salt is administered orally once daily on a continuous dosing schedule starting on day 1 in combination with once weekly paclitaxel at a dose of 80 mg/m$^2$ (days 1, 8, 15, and 22) on a 28-day cycle. COMPOUND A or its hydrochloride salt is administered at a dose of 100 mg Compound A free-base.

Paclitaxel is administered by intravenous infusion. Paclitaxel is supplied as multi-dose vials for injection. Paclitaxel is diluted using 0.9% sodium chloride injection, USP; 5% dextrose injection, USP; 5% dextrose and 0.9% sodium chloride injection, USP, or 5% dextrone in Ringer's injection to a final concentration of 0.3 to 1.2 mg/mL. Paclitaxel is administered every week as 1-hour (±15 minutes) IV infusion after standard premedication on Day 1 of every cycle. Prior to administration of paclitaxel, patients are pre-medicated according to the standard institutional practice or the product label to prevent severe hypersensitivity reactions. Anti-hypersensitivity therapy may be administered prior to the ECG of each cycle. Options include: Dexamethasone: 20 mg orally administered 12 and 6 hours prior to start of paclitaxel administration, or diphenhydramine (or equivalent): 50 mg IV administered by IV approximately 30-60 minutes prior to start of paclitaxel administration, or ranitidine: 50 mg IV administered approximately 30-60 minutes prior to the start of paclitaxel administration, or cimetidine: 300 mg IV administered approximately 30-60 minutes prior to start of paclitaxel administration. Cimetidine should be administered as a single dose and only if no alternative can be found. If hypersensitivity occurs during the administration of paclitaxel, the following treatment guidelines may be followed:

For mild symptoms (e.g., mile flushing, rash, pruritus) it is possible to complete the infusion under close supervision For moderate symptoms (e.g., moderate rash, flushing, mild dyspnea, chest discomfort, mild hypotension): (1) Stop the paclitaxel infusion and give diphenhydramine 25-50 mg IV and methylprednisolone 125 mg IV, (2) Once symptoms have resolved, resume paclitaxel infusion at a rate of 10% of original rate for 15 minutes, then at 25% of original rate for 15 minutes. If no further symptoms develop, continue at original rate until infusion is complete.

For severe symptoms (e.g., one or more of: respiratory distress requiring treatment, generalized urticaria, angioedema, hypotension requiring therapy): (1) Stop the paclitaxel infusion and give diphenhydramine and methylprednisone as above. Use epinephrine or bronchodilators, if indicated, or (2) Do not rechallenge the patient with paclitaxel.

COMPOUND A-matching placebo will be administered orally once daily on a continuous dosing schedule starting on day 1.

Treatment is continued until disease progression (radiologically confirmed according to RECIST v1.1) or until discontinuation for any other reason. A complete treatment cycle is defined as 28 calendar days during which COMPOUND A or its hydrochloride salt or its placebo is given once daily and paclitaxel is given once weekly. The last day of complete treatment cycle is day 29. Day 1 of the next cycle starts on day 29. Efficacy and safety monitoring are conducted regularly. Tumor assessments are performed 4 weeks after study treatment start and afterwards every 6 weeks until radiological progression.

Efficacy and tumor response is determined according to specific guidelines on the Response Evaluation Criteria in Solid Tumors (RECIST), based on RECIST version 1.1.

Safety is monitored by physical examination, vital signs, weight, performance status evaluation, ECG, cardiac imaging, laboratory evaluations including glucose monitoring and assessments of patient rated mood scales as well as adverse events (serious and non-serious).

Patients requiring a COMPOUND A or its hydrochloride salt or placebo dose delay of >28 days will be permanently discontinued from the study drug. Grade 4 adverse events will result in permanent discontinuation irrespective of recovery time. Further, a maximum of 3 dose reductions of COMPOUND A or its hydrochloride salt are allowed as follows and each dose reflects the dose amount of the Compound A free base:

| Compound A or its hydrochloride salt/placebo dose levels and dose reductions* | |
| --- | --- |
| Starting dose level | 100 mg/day continuously |
| Dose level-1 | 80 mg/day continuously |
| Dose level-2 | 100 mg/day 5 days out of 7 |
| Dose level-3 | 80 mg/day 5 days out of 7** |

*Dose reduction should be based on the worst preceding toxicity

**Dose reduction below 80 mg/day 5 days out of 7 is not allowed. If a dose reduction below dose level-3 is required, the patient should be permanently discontinued from COMPOUND A/placebo.

A change from continuous schedule to intermittent (5 days out of 7) is preceded by 2 days without COMPOUND A treatment. Dose modifications and dose interruption are permitted with the following guidelines:

| Worst toxicity (CTCAE 4.03 Grade) | Dose Modifications for COMPOUND A or its hydrochloride salt/placebo |
| --- | --- |
| HEMATOLOGICAL | |
| Neutropenia (ANC) | |
| Grade 1 (ANC < LLN-1.5 × 10$^9$/L) | Maintain dose level |
| Grade 2 (ANC < 1.5-1.0 × 10$^9$/L) | |
| Grade 3 (ANC < 1.0-0.5 × 10$^9$/L) | Omit dose until resolved to ≤ Grade 1, then: |
| Grade 4 (ANC < 0.5 × 10$^9$/L) | If resolved in ≤7 days, then maintain dose level<br>If resolved in >7 days, then ↓ 1 dose level |
| Febrile neutropenia (ANC < 1.0 × 10$^9$/L, with a single temperature of ≥38.3° C. or a sustained temperature of ≥38° C. for more than one hour) | Omit dose until resolved, then ↓ 1 dose level |
| Thrombocytopenia | |
| Grade 1 (PLT < LLN-75 × 10$^9$/L) | Maintain dose level |
| Grade 2 (PLT < 75-50 × 10$^9$/L) | |
| Grade 3 (PLT < 50-25 × 10$^9$/L) | Omit dose until resolved to ≤ Grade 1, then:<br>If resolved in ≤7 days, then maintain dose level<br>If resolved in >7 days, then ↓ 1 dose level |
| Grade 4 (PLT < 25 × 10$^9$/L) | Omit dose until resolved to ≤ Grade 1, then, ↓ 1 dose level |
| RENAL | |
| Serum creatinine | |
| Grade 1 (<2 × ULN) | Maintain dose level |
| Grade 2 (2-3 × ULN) | Omit dose until resolved to ≤ grade 1, then:<br>If resolved in ≤7 days, then maintain dose level<br>If resolved in >7 days, then ↓ 1 dose level |
| Grade 3 (>3.0-6.0 × ULN) | Permanently discontinue patient from COMPOUND A/placebo |
| Grade 4 (>6.0 × ULN) | Permanently discontinue patient from COMPOUND A/placebo |
| HEPATIC | |
| Bilirubin (*for patients with Gilbert Syndrome these dose modifications apply to changes in direct bilirubin only) will be fractionated if elevated | |
| Grade 1 (>ULN-1.5 × ULN) | Maintain dose level with LFTs* monitored as per protocol |
| Grade 2 (>1.5-3.0 × ULN) with ALT or AST ≤ 3.0 × ULN | Omit dose until resolved to ≤ Grade 1, then:<br>If resolved in ≤7 days, then maintain dose level<br>If resolved in >7 days, then ↓ 1 dose level |
| Grade 3 (>3.0-10.0 × ULN) with ALT or AST ≤ 3.0 × ULN | Omit dose until resolved to ≤ Grade 1, then:<br>If resolved in ≤7 days, ↓ 1 dose level<br>If resolved in >7 days discontinue patient from COMPOUND A/placebo |

-continued

| Worst toxicity (CTCAE 4.03 Grade) | Dose Modifications for COMPOUND A or its hydrochloride salt/placebo |
|---|---|
| Grade 4 (>10.0 × ULN) | Permanently discontinue patient from COMPOUND A/placebo |

AST or ALT

| | |
|---|---|
| Grade 1 (>ULN-3.0 × ULN) | Maintain dose level with LFTs* monitored per protocol |
| Grade 2 (>3.0-5.0 × ULN) without total bilirubin elevation to >2.0 × ULN | Omit dose until resolved to ≤ Grade 1, then If resolved in ≤7 days, then maintain dose level If resolved in >7 days, then ↓ 1 dose level |
| Grade 3 (>5.0-20.0 × ULN) without total bilirubin elevation to >2.0 × ULN | Omit dose until resolved to ≤ Grade 1, then If resolved in ≤7 days, then maintain dose level If resolved in >7 days, then ↓ 1 dose level |
| Grade 4 (>20.0 × ULN) without bilirubin elevation to >2.0 × ULN | Omit dose until resolved to ≤ Grade 1, then ↓ 1 dose level |

AST or ALT and concurrent Bilirubin

| | |
|---|---|
| AST or ALT > 3.0 × ULN and total bilirubin >2.0 × ULN | Permanently discontinue COMPOUND A/placebo |

*(LFTs include albumin, ALT, AST, total bilirubin (fractionated if total bilirubin >2.0 × ULN), alkaline phosphatase (fractionated if alkaline phosphatase is grade 2 or higher) and GGT)
Hepatic toxicity monitoring (*for patients with Gilbert Syndrome: total and direct bilirubin must be monitored, intensified monitoring applies to changes in direct bilirubin only; the monitoring includes the following LFTs: albumin, ALT, AST, total bilirubin (fractionated if total bilirubin >2.0 × ULN), alkaline phosphatase (fractionated if alkaline phosphatase is grade 2 or higher) and GGT):
Cycle 1 and 2: every other week (if visit schedule allows a more frequent monitoring this should be considered) or more frequently if clinically indicated especially for patients with borderline acceptable AST/ALT/bilirubin* values
Cycle 3 and onward: monthly or more frequently if clinically indicated
In case of any occurrence of ALT/AST/bilirubin* increase ≥ grade 2 the liver function tests must be monitored weekly or more frequently if clinically indicated until resolved to ≤ grade 1
In case of any occurrence of ALT/AST/bilirubin* increase ≥ grade 3 the liver function tests must be monitored weekly or more frequently if clinically indicated until resolved to ≤ grade 1; hereafter the monitoring should be continued every other week or more frequently if clinically indicated until the end of treatment with study medication
Patients who discontinued study treatment should be monitored weekly, including LFTs* or more frequently if clinically indicated until resolved to ≤ grade 1 or stabilization (no CTCAE grade change over 4 weeks).

ENDOCRINE/METABOLIC

Fasting Plasma Glucose (FPG)

| | |
|---|---|
| Grade 1 (>ULN-160 mg/dL) [>ULN-8.9 mmol/L] | Maintain dose level, check FPG every week initiate or intensify medication with appropriate anti-diabetic treatment as per investigator's discretion instruct patient to follow dietary guidelines according to local and/or institutional standards for management of diabetes mellitus (such as those provided by the American Diabetes Association) during the study consider use of oral anti-hyperglycemic therapy such as metformin (or intensify existing medications) check FPG at least weekly for 8 weeks, then continue checking at least every 2 weeks |
| Grade 2 (>160-250 mg/dL) [>8.9-13.9 mmol/L] | If asymptomatic, maintain dose and re-check FPG within 24 hours. If grade worsens or improves then follow specific grade recommendations. If FPG remains at Grade 2: maintain dose level and monitor FPG at least weekly until FPG resolves to ≤ Grade 1 initate or intensify medication with appropriate anti-diabetic treatment such as metformin; consider adding a second oral agent if no improvement after several days instruct patient to follow dietary guidelines according to local and/or institutional standards for management |

-continued

| Worst toxicity (CTCAE 4.03 Grade) | Dose Modifications for COMPOUND A or its hydrochloride salt/placebo |
|---|---|
| Grade 3 (>250-500 mg/dL) [>13.9-27.8 mmol/L] | of diabetes mellitus (such as those provided by the American Diabetes Association) during the study<br>If FPG does not resolve to ≤ Grade 1 within 14 days after institution of appropriate anti-diabetic treatment reduce COMPOUND A/placebo by 1 dose level<br>Continue with anti-diabetic treatment and check FPG at least weekly for 8 weeks, then continue checking at least every 2 weeks<br>Omit COMPOUND A/placebo, initiate or intensify medication with appropriate anti-diabetic treatment, re-check FPG within 24 hours. If grade worsens or improves then follow specific grade recommendations.<br>If FPG remains at Grade 3:<br>administer intravenous hydration and intervention for electrolyte/ketoacidosis/hyperosmolar disturbances as clinically appropriate<br>continue to omit COMPOUND A/placebo<br>monitor FPG at least twice weekly until FPG resolves to ≤ Grade 1<br>If FPG resolves to ≤ Grade 1 in 7 days or less, then re-start COMPOUND A/placebo and ↓ 1 dose level<br>If FPG remains greater than Grade 1 severity for more than 7 days, then discontinue patient from COMPOUND A/placebo<br>initiate or continue anti-diabetic treatment as appropriate<br>instruct patient to follow dietary guidelines according to local and/or institutional standards for management of diabetes mellitus (such as those provided by the American Diabetes Association) during the study<br>consider use of oral anti-hyperglycemic therapy such as metformin<br>check FPG at least weekly for 8 weeks, then continue checking at least every 2 weeks<br>For non-fasting plasma glucose >250-500 mg/dL (>13.9-27.8 mmol/L) accompanied by signs/symptoms of hyperglycemia (for example, mental status changes, excessive thirst, polyuria), or presence of blood or urine ketones, omit Compund A/placebo and following guidance for management of Grade 3 fasting plasma glucose (FPG) |
| Grade 4 (>500 mg/dL) [≥27.8 mmol/L] | Immediately omit Compound/placebo, initiate or intensify medication with appropriate anti-diabetic treatment, re-check within 24 hours. If grade improves then follow specific grade recommendations.<br>If FPG is confirmed at Grade 4:<br>administer intravenous hydration and intervention for electrolyte/ketoacidosis/hyperosmolar disturbances as clinically appropriate<br>discontinue patient from Comopund A/placebo<br>instruct patient to follow dietary guidelines according to local and/or institutional standards for management of diabetes mellitus (such as those provided by the American Diabetes Association) during the study<br>consider use of oral anti-hyperglycemic therapy such as metformin<br>check FPG at least weekly for 8 weeks, then continue checking at least every 2 weeks if clinically indicated<br>For non-fasting plasma glucose >500 mg/dL (>27.8 mmol/L) accompanied by signs/symptoms of hyperglycemia (for example, mental status changes, excessive thirst, polyuria), or presence of blood or urine ketones, discontinue Compound A and following guidance for management of Grade 4 fasting plasma glucose (FPG). |
| CARDIAC ||
| Cardiac-Left Ventricular systolic dysfunction ||
| Asymptomatic, resting ejection fraction 40-50%; or 10-20% drop from baseline | Maintain dose level, and continue COMPOUND A with caution<br>Repeat LVEF within 4 weeks or as clinically appropriate |

| Worst toxicity (CTCAE 4.03 Grade) | Dose Modifications for COMPOUND A or its hydrochloride salt/placebo |
|---|---|
| Symptomatic, responsive to intervention, ejection fraction 20-39% or >20% drop from baseline | Omit COMPOUND A/placebo until resolved* (as defined below), then ↓ 1 dose level<br>LVEF measurement to be repeated, if not resolved* within 3 weeks, permanently discontinue patient from COMPOUND A treatment<br>*the event is considered resolved when the patient is asymptomatic, has a resting ejection fraction ≥40% and ≤20% decrease from baseline |
| Refractory or poorly controlled, ejection fraction <20% | Permanently discontinue patient from COMPOUND A/placebo |

Cardiac-QTc prolongation

| | |
|---|---|
| QTcF >500 ms (≥Grade 3) or >60 ms change from baseline on at least two separate ECGs | First Occurrence:<br>omit COMPOUND A/placebo<br>Perform an analysis of serum potassium and magnesium, and if below lower limit of normal, correct with supplements to within normal limits. Concomitant medication usage must be reviewed.<br>Perform a repeat ECG within one hour of the first QTcF of >500 ms or >60 ms from baseline<br>If QTcF remains >500 ms or >60 ms from baseline, repeat ECG as clinically indicated, but at least once a day until the QTcF returns to <480 ms. Seek cardiologist input.<br>Once QTcF prolongation has resolved, COMPOUND A/placebo may be restarted at a one lower dose level<br>Second Occurrence:<br>Permanently discontinue patient from COMPOUND A/placebo |
| Other Cardiac Events | |
| Grade 1 or 2 | Maintain dose level |
| Grade 3 | Omit dose until resolved to ≤ Grade 1, then ↓ 1 dose level |
| Grade 4 | Permanently discontinue patient from COMPOUND A/placebo |

OTHER

Mood alteration

*Note:
For all grades, if question 9 on the PHQ-9 has a positive response (as indicated by selecting "1", "2", or "3"), omit study drug and refer patient for psychiatric consult regardless of the total questionnaire score or CTCAE grading to confirm if study drug should be interrupted or permanently discontinued.

| | |
|---|---|
| Grade 1* | Maintain dose level<br>Consider psychiatric consultation at the investigator's discretion and introduce optimal management |
| Grade 2* | Omit dose until resolved to ≤ Grade 1, or baseline status<br>Consider psychiatric consultation at the investigator's discretion and introduce optimal management<br>First event: if the condition resolved to Grade ≤ 1 or to baseline status, continue to co-medicate and then maintain dose level<br>Second and further events: if the condition resolved to Grade ≤ 1 or to baseline status, continue to co-medicate and then ↓ 1 dose level |
| Grade 3* | Omit dose until resolved to ≤ Grade 1, or baseline status<br>Psychiatric consultation is required and introduce optimal management<br>If the condition resolved to Grade ≤ 1 or to baseline status, continue to co-medicate and then then ↓ 1 dose level |
| Grade 4* | Permanently discontinue patient from COMPOUND A/placebo<br>Psychiatric consultation is required and introduce optimal management |

Rash

| | |
|---|---|
| Grade 1 | Maintain dose level. Consider to initiate appropriate skin toxicity therapy (such as antihistamines, topical corticosteroids) |

-continued

| Worst toxicity (CTCAE 4.03 Grade) | Dose Modifications for COMPOUND A or its hydrochloride salt/placebo |
|---|---|
| Grade 2 | First occurrence: Omit dose until resolved to Grade ≤ 1 then:<br>If resolved in ≤2 weeks, maintain dose level.<br>If resolved in more than 2 weeks, ↓ 1 dose level.<br>Second occurrence: ↓ 1 dose level<br>Initiate/intensify appropriate skin toxicity therapy (such as antihistamines, topical corticosteroids) |
| Grade 3 | First Occurrence: Omit dose until resolved to CTCAE Grade ≤ 1; then ↓ 1 dose level.<br>Second Occurrence: permanently discontinue patient from COMPOUND A/placebo<br>According to the investigators discretion, a paired skin biopsy could be obtained (from both an affected and an unaffected skin area for local histopathology assessment) if clinical appropriate. |
| Grade 4 | Permanently discontinue patient from COMPOUND A/placebo<br>According to the investigators discretion, a paired skin biopsy could be obtained (from both an affected and an unaffected skin area for local histopathology assessment) if clinical appropriate. |
| Fatigue (asthenia) | |
| Grade 1 or 2 | Maintain dose level |
| Grade 3 | Omit dose until resolved to ≤ Grade 1, then:<br>If resolved in ≤7 days, maintain dose level<br>If resolved in >7 days, ↓ 1 dose level |
| Pneumonitis | Grade 1: Administer of dose.<br>Grade 2: Reduce COMPOUND A/placebo by 1 dose level until recovery to < Grade 1. Study treatment may be interrupted. Patients will discontinue if they fail to recover to < Grade 1 within 3 weeks.<br>Grade 3: Hold treatment with COMPOUND A/placebo until recovery to < Grade 1. May restart study treatment within 3 weeks at a reduced dose level (by one level) if evidence of clinical benefit.<br>Grade 4: Discontinue treatment with COMPOUND A/placebo. |
| Stomatitis/Oral mucositis | |
| Grade 1/Tolerable Grade 2 | Maintain dose level. Non alcoholic or salt water mouth wash |
| Intolerable Grade 2 or Grade 3 | First occurrence: hold until ≤ G1 and ↓ 1 dose level (if stomatitis is readily manageable with optimal management, re-introduction at the same level might be considered at the discretion of the investigator).<br>Second occurrence: hold until ≤ G1 and ↓ 1 dose level. |
| Grade 4 | Permanently discontinue patient from COMPOUND A/placebo |
| Other non-hematological adverse events | |
| Grade 1 or 2 | Maintain dose level |
| Grade 3 | Omit dose until resolved to ≤ Grade 1, then ↓ 1 dose level |
| Grade 4 | Permanently discontinue patient from COMPOUND A/placebo |

Note:
Omit dose for ≥ Grade 3 vomiting or Grade 3 nausea only if the vomiting or nausea cannot be controlled with optimal antiemetic Dose modifications for paclitaxel are permitted for adverse events suspected to be caused by paclitaxel. The following guidelines should be considered:
Paclitaxel should be administered only if ANC>1.500/mm3 (1.5×10$^9$/L) and platelets >100.000/mm3 (100× 10$^9$/L).
In case of a life-threatening event, consider discontinuing paclitaxel
In case of grade 3 or 4 AEs despite medical management:
Hold paclitaxel until the event has resolved to grade 1 or better, then re-introduce at the reduced dose.
In case of a second episode of the same event at grade 3 or 4, consider discontinuing paclitaxel
In cases of grade 2 non-hematologic AE (except alopecia) that are persistent despite medical management, consider holding paclitaxel until event resolves to grade 1 or better, then re-introduce at a reduced dose.
The minimum paclitaxel dose allowed on study and the first dose reduction level is 65 mg/m$^2$ (i.e. only one dose reduction of paclitaxel is permitted to 65 mg/m$^2$).
Additionally, paclitaxel should be dose adjusted as needed, in accordance with local prescribing information and practice.
Concomitant therapy necessary for care of the patient is permitted except:

Systemic corticosteroid treatment is not permitted except for topical applications, inhaled sprays, eye drops or local injections; systemic corticosteroids ≤anti-inflammatory potency of 4 mg dexamethasone; or as premedication for pacliataxel;

Drugs metabolized by CYP450 enzymes must be monitored;

Certain non-enzyme inducing anti-epileptic drugs

Other anticancer therapy or other investigational therapies are not permitted

Prophylactic use of hematopoietic growth factors are not permitted. Permitted in case of emergency.

Therapeutic doses of warfarin sodium or any other coumarin-derivative anticoagulants are not permitted.

Enzyme-inducing anti-epileptic drug is not permitted.

Drugs with a known risk for Torsades de Pointes are not permitted.

Moderate and strong CYP3A inhibitors are not permitted.

Herbal preparations/medications are not permitted.

Patients may be withdrawn from the study if any of the following occur: adverse event, lost to follow-up, non-compliance with study treatment, physician decision, pregnancy, progressive disease, protocol deviation, study terminated by sponsor, technical problems, subject/guardian decision, death. Patients must be discontinued if any of the following occur: adjustment to study treatment that results in discontinuation, use of prohibited medication, interruption of study treatment for >28 days from intended day of next scheduled dose.

All patients who discontinue from study treatment due to disease progression must have their progression clearly documented according to the criteria specified in RECIST v1.1. If a patient did not discontinue study treatment due to disease progression, death, start of new anti-neoplastic therapies, lost to follow-up, or withdrawal of consent to efficacy follow-up, then tumor assessments should continue to be performed every 6 weeks until the start of new anti-cancer therapy, disease progression, death, lost to follow-up or withdrawn consent to efficacy follow-up.

In addition, all new anticancer therapies given after the last dose of the study treatment, until disease progression, death, lost to follow-up, or withdrawal of consent will be recorded in the electronic Case Report Forms (eCRFs).

After discontinuation of treatment, all patients will be contacted for safety evaluations (i.e, assessment of adverse events and/or serious adverse events, concomitant medications) for 30 days after the last dose of study treatment. Patients whose treatment is interrupted or permanently discontinued due to an adverse event are followed at least once a week for 4 weeks and subsequently at 4-weeks intervals until resolution or stabilization of the event, whichever comes first.

For patients that do not discontinue study treatment due to disease progression, death, start of new anti-neoplastic therapies, lost to follow-up, or withdrawal of consent to efficacy follow-up, tumor assessments are performed every 6 weeks until the start of new anti-cancer therapy, disease progression, death, lost to follow-up or withdrawn consent to efficacy follow-up.

All patients are followed for survival status every 3 months regardless of treatment discontinuation reason until death, lost to follow-up or withdrawal of consent to survival follow-up. Prior to collecting survival information, end of post-treatment information is collected at study phase completion (i.e., adverse event, lost to follow-up, physician decision, pregnancy, protocol deviation, technical problems, subject/guardian decision, death, new therapy for study indication, progressive disease, study termination by sponsor).

What is claimed is:

1. A method of treating a squamous cell carcinoma of the head and neck comprising administering a jointly therapeutically effective amount of the pharmaceutical combination comprising (a) a compound of formula (I)

or a pharmaceutically acceptable salt thereof, and (b) paclitaxel or a pharmaceutically acceptable salt thereof, to a subject in need thereof, wherein the compound of formula (I) or its pharmaceutically acceptable salt is administered to the subject in a dose amount ranging from about 60 mg/day to about 120 mg/day in an adult human.

2. The method according to claim 1, wherein the paclitaxel is administered to the subject in a dose amount ranging from approximately about 15 to 200 mg/m$^2$ per week in an adult human.

3. The method according to claim 1 wherein the cancer of the head and neck is resistant to prior treatment with paclitaxel, fluorouracil (5-FU), platinum-based therapies, or a combination thereof.

* * * * *